US012758248B2

(12) United States Patent
Gabrick et al.

(10) Patent No.: US 12,758,248 B2
(45) Date of Patent: Oct. 13, 2026

(54) ENDOSCOPIC RETINACULATOME

(71) Applicant: VANDERBILT UNIVERSITY, Nashville, TN (US)

(72) Inventors: Kyle Gabrick, Nashville, TN (US); Brian Drolet, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 279 days.

(21) Appl. No.: 18/686,663

(22) PCT Filed: Aug. 25, 2022

(86) PCT No.: PCT/US2022/075462
§ 371 (c)(1),
(2) Date: Feb. 26, 2024

(87) PCT Pub. No.: WO2023/028560
PCT Pub. Date: Mar. 2, 2023

(65) Prior Publication Data

US 2024/0374279 A1 Nov. 14, 2024

Related U.S. Application Data

(60) Provisional application No. 63/296,683, filed on Jan. 5, 2022, provisional application No. 63/236,930, filed on Aug. 25, 2021.

(51) Int. Cl.
*A61B 17/32* (2006.01)
*A61B 17/00* (2006.01)

(52) U.S. Cl.
CPC ................. *A61B 17/320036* (2013.01); *A61B 2017/00115* (2013.01)

(58) Field of Classification Search
CPC .. A61B 17/320036; A61B 2017/00115; A61B 1/00097; A61B 1/00098; A61B 1/00087; A61B 1/00096
See application file for complete search history.

(56) References Cited

U.S. PATENT DOCUMENTS 5,836,869 A 11/1998 Kudo et al.
2006/0155209 A1* 7/2006 Miller .................. A61B 10/025 600/566

(Continued)

OTHER PUBLICATIONS

International Search Report and Written Opinion, PCT/US2022/075462, mailed Nov. 22, 2024.

*Primary Examiner* — Timothy J Neal
(74) *Attorney, Agent, or Firm* — Thomas Horstemeyer LLP.

(57) ABSTRACT

Various embodiments of a self-contained endoscopic surgical instrument, kit, and system are described. In one example, the endoscopic surgical instrument includes a blade complex and a dilating head. The blade complex having a blade secured within a blade guard such that a cutting edge of the blade is exposed. The blade guard having a superior portion that covers a top edge of the blade and projects over the cutting edge of the blade. The dilating head including a main body having a blade seat and configured to house a camera and a light source. The blade seat is configured to receive and secure the removable blade complex. The device also includes a handle configured to house a controller, a video processor, a video transmitter, and a power source.

20 Claims, 3 Drawing Sheets

(56) References Cited

U.S. PATENT DOCUMENTS

| | | | | |
|---|---|---|---|---|
| 2007/0255296 | A1* | 11/2007 | Sauer | A61B 17/30 606/144 |
| 2008/0195128 | A1* | 8/2008 | Orbay | A61B 1/00048 600/183 |
| 2008/0255600 | A1* | 10/2008 | Braam | A61B 17/320036 606/190 |
| 2013/0046199 | A1* | 2/2013 | Dubois | A61B 17/32002 600/566 |
| 2015/0048139 | A1 | 2/2015 | Penna et al. | |
| 2016/0210411 | A1* | 7/2016 | Mentis | G06F 3/0304 |
| 2017/0215909 | A1 | 8/2017 | Klotz et al. | |
| 2018/0058851 | A1 | 3/2018 | Amling et al. | |
| 2020/0375585 | A1* | 12/2020 | Swayze | A61B 18/1445 |

* cited by examiner

ENDOSCOPIC RETINACULATOME

CROSS-REFERENCE TO RELATED APPLICATIONS

This application is a U.S. National Stage patent application claiming priority to PCT/US2022/075462 filed Aug. 25, 2022 which claims the benefit of and priority to U.S. Provisional Application No. 63/236,930, filed Aug. 25, 2021, and U.S. Provisional Application No. 63/296,683, filed Jan. 5, 2022, the entire contents of which are hereby incorporated by reference in their entirety.

BACKGROUND

Carpal tunnel syndrome is the most common compressive neuropathy, which affects 3-8% of the population. The standard of care for treatment is nerve decompression performed through an open incision or with an endoscopic technique. Carpal tunnel release is performed about 500,000 times annually in the United States. Thick bands of fascia located under the subcutaneous tissues can be cut with a surgical instrument to release pressure on the nerve as a treatment for carpal tunnel syndrome.

SUMMARY

A self-contained endoscopic medical device, instrument kit, and system is described. In one example, a medical device can include a blade complex and a dilating head. The blade complex can include a blade and a blade guard. The blade secured within the blade guard such that a cutting edge of the blade is exposed. The blade guard having a superior portion that covers a top edge of the blade and projects over the cutting edge of the blade, the top edge being perpendicular to the cutting edge. The device also includes a dilating head comprising a main body having a blade seat. The main body of the dilating head configured to house a camera and a light source. The blade seat configured to receive and secure the blade complex with the blade defining a center plane of the dilating head. The device also includes an arm attached to a proximal end of the dilating head. The device also includes a handle configured to house a controller, a video processor, a video transmitter, and a power source, the controller operatively connected to the camera and the light source via the arm attached to the handle.

In additional aspects, the main body of the medical device can include a base and a distal portion extending distally at an angle with respect to the base. At least a portion of the blade seat can extend into the base such that, when seated, the blade is substantially perpendicular to the base and the cutting edge of the blade faces the distal portion. The camera can be positioned in the distal portion configured with a field of view of the cutting edge of the blade. The distal portion can include a distal tip having a blunt end. The distal portion can be contoured to provide a smooth transition to the base of the main body. The distal portion further can include a scraper on a superior surface of the distal portion. The main body further can include a pair of fairings extending laterally from the base, the pair of contoured fairings on opposite sides of the base symmetrical about the center plane. At least a portion of the contoured fairings extend away from the blade seat forming a concave surface on the main body opposite the blade seat. The main body further can include a pair of contoured flanges protruding from the base. The pair of contoured flanges can be positioned on opposite sides of the distal portion symmetrical about the center plane. The main body can include a medical grade polymer. The main body can include a translucent material.

In additional aspects, the light source of the medical device can be a pair of light sources positioned symmetrically about the center plane. The light source can be at least one led or at least one fiber optic strand. The blade guard of the blade complex is contoured and configured to act as a spacer from the blade. The blade complex can be detachably attached and replaceable. In some examples, the dilating head can be detachably attached to the arm. The dilating head of the medical device can be one of a plurality of dilating heads and replaceable, where individual ones of the plurality of dilating heads are configured with predetermined dimensions and interchangeably attachable to the arm of the medical device. In some examples, the dilating head can be attached to the arm and the arm is detachably attached to the handle. In some cases, the arm can have a predefined length. In some cases, the arm can be configured with a bend. In some cases, an angle formed by the bend can be adjustable. In some examples, the controller is configured to operate the light source and the camera. The camera captures video and the video is transmitted wirelessly to a client device. In some cases, the controller is configured to adjust the white balance of the camera. In some cases, the controller is configured to adjust the zoom and focus of the camera.

In another example, an endoscopic instrument kit can include: the medical device and a plurality of dilating heads, the dilating head of the medical device being one of a plurality of dilating heads and replaceable, individual ones of the plurality of dilating heads configured with predetermined dimensions and interchangeably attachable to the arm of the medical device.

In another example, an endoscopic instrument system, may include: the medical device and at least one computing device that may include at least one hardware processor; program instructions stored in memory and executable by the at least one computing device that, when executed, direct the at least one computing device to: access real-time video data from the camera of the medical device; and display the real-time video data on a display. In some cases, the at least one computing device is further directed to execute instructions to obtain video images, transmit video images, control white balance of the video, control zoom and focus of the camera, or a combination thereof. In some cases, the at least one computing device is further directed to execute instructions to adjust the brightness of the light source. The medical device may further include a communication module configured for wireless communication with the at least one computer. Other embodiments of this aspect include corresponding computer systems, apparatus, and computer programs recorded on one or more computer storage devices, each configured to perform the actions of the methods.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF DRAWINGS

Many aspects of the present disclosure can be better understood with reference to the following drawings. The components in the drawings are not necessarily drawn to scale, with emphasis instead being placed upon clearly illustrating the principles of the disclosure. In the drawings, like reference numerals designate corresponding parts throughout several views.

DETAILED DESCRIPTION

Figure 1:
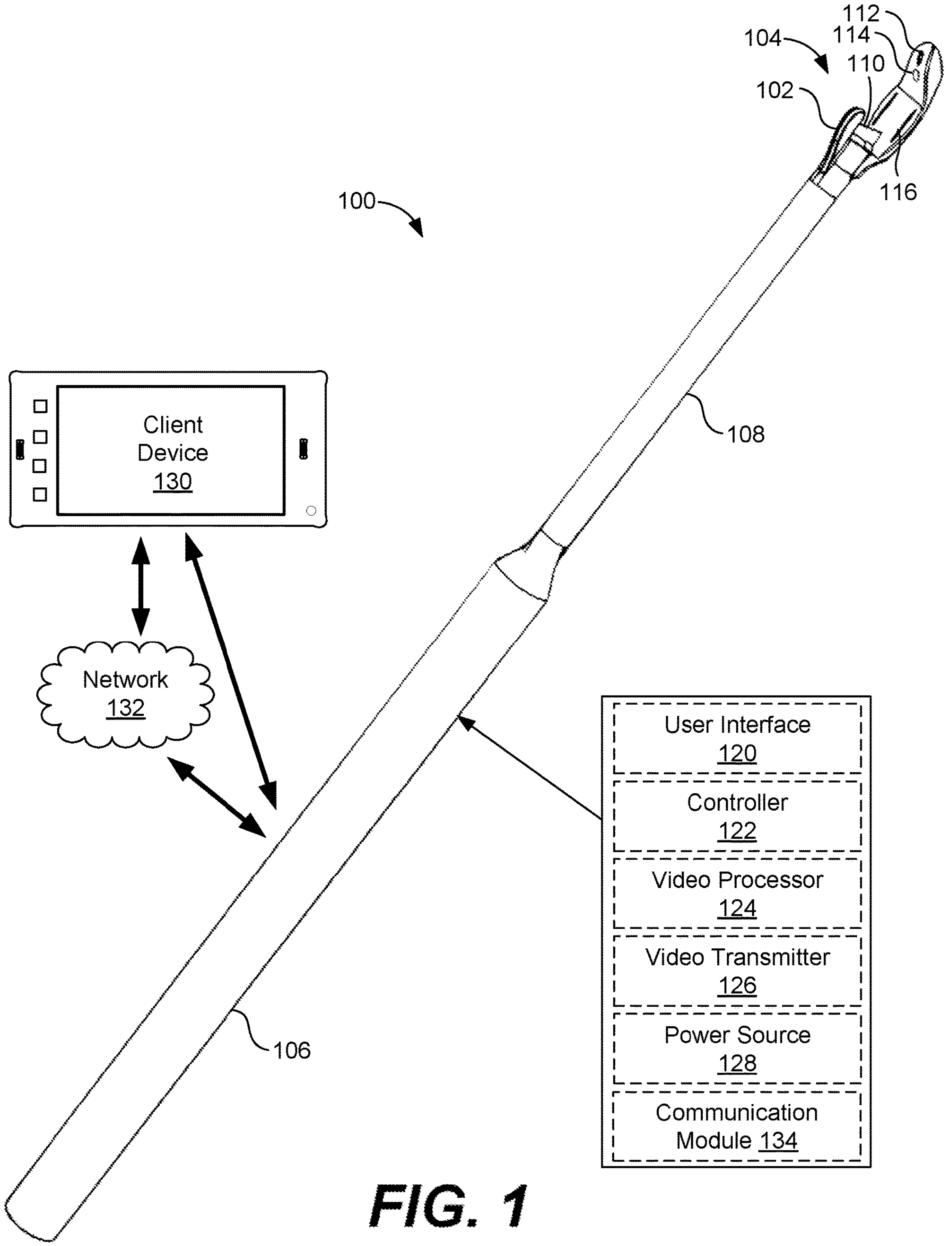
FIG. 1 illustrates an example of an endoscopic retinaculatome device according to various embodiments described herein.

Traditional endoscopic carpal and cubital tunnel devices can be overly complex, with moving parts and many cables for external (and technologically obsolete) video and lighting devices. The endoscope provides a camera that allows a surgeon to see structures below the skin through a minimally invasive approach. The endoscope is placed through a small incision, which avoids the need for a large incision to open the entire area. The surgical instruments are also inserted with the endoscope or through small incisions in the wrist or in the wrist and palm. During endoscopic carpal tunnel release surgery, the transverse carpal ligament is cut to release pressure on the median nerve (i.e., decompression), relieving carpal tunnel syndrome symptoms.

Traditional endoscopic techniques utilize an endoscopic tower that is necessary to provide an endoscope video imaging of the surgical area. However, the equipment is expensive, bulky, and only available in limited locations or shared within a hospital. This limits implementation of an endoscopic procedure to only the facilities that can afford the equipment and have availability based on the schedule. To overcome this limitation, there is a need for a compact, portable device that is simple to use and re-use to allow for endoscopic carpal tunnel release surgery without reliance on an endoscopic tower. This frees the surgical device from expensive hospital infrastructure and allows for use in operating facilities that do not have an endoscopic tower.

In the context outlined above, various examples of an endoscopic retinaculatome are disclosed herein. The endoscopic retinaculatome (ERT) is a self-contained endoscopic surgical instrument used to transect subcutaneous fascial structures for the treatment of compressive neuropathies and compartment syndromes. The ERT provides the surgeon with significant advantages when compared with similar endoscopic devices. It does not rely on external lighting and video sources which require physical cords to be passed from the sterile to non-sterile areas of the operating room. A stand-alone device such as the ERT in combination with a tablet the surgeon can safely utilize the instrument without reliance on specialized support equipment (such as external power, lighting, and video cables) with lower risks of contamination of the sterile operating field. Furthermore, the elimination of specialized equipment (external power, lighting, and video equipment) will allow for more widespread implementation of the device to underserved clinics throughout the United States and abroad.

The endoscopic retinaculatome is an endoscopic medical device for cutting fascia located under the subcutaneous tissues that includes a protected surgical blade and integrated video technology. The endoscopic retinaculatome can be used to pass below the skin to identify and cut tissue such as the transverse carpal ligament in carpal tunnel surgery and the fascia in compartment release surgery. The stand-alone medical device is compact and handheld, eliminating the need for an endoscopic tower as well as any cables that are unwieldy. The head of the device can be detachable to allow for a replacement head or specialized head for a particular surgery. The device can be sterilized, and the protected surgical blade can be replaced for each surgery. The protected surgical blade of the endoscopic retinaculatome is designed to cut thick bands of tissue located under the subcutaneous tissues, such as in fasciotomy, escharotomy with common application to, carpal tunnel, cubital tunnel, treatment of compartment syndrome, and similar conditions. The head of the device provides a seat for the protected surgical blade and includes a novel tip configuration that cradles and protects neurovascular structures while the device is being used.

The endoscopic retinaculatome includes an imaging device and light source, thus does not rely on external lighting and video sources. The endoscopic retinaculatome can be configured to transmit the acquired video or images to a computing device for real-time display and/or image capture. In an example, the endoscopic retinaculatome can be configured to interface with a client device such as a wireless tablet or other computing device provided with a monitor to display the transmitted images or real-time imaging. A system comprising the endoscopic retinaculatome and computing device is also less complex for the operating room staff to assemble, making it more accessible for remote clinics around the world that cannot afford or access an endoscopic tower.

The endoscopic retinaculatome provides the surgeon with significant advantages when compared with similar endoscopic devices. It does not rely on external lighting and video sources that require physical cords to be passed from the sterile to non-sterile areas of the operating room. For example, using a stand-alone system such as the endoscopic retinaculatome in combination with a tablet, the surgeon can safely utilize the instrument without reliance on specialized support equipment (e.g., external power, lighting, or video cables), thus lowering the risks of contamination of the sterile operating field. The endoscopic retinaculatome has a unique cutting tip that does not rely on moving parts. Further, the device increases the tactile feedback while being designed with a camera, lateral fairings, and a concave undersurface to protect neurovascular structures.

The endoscopic retinaculatome can include at least one hardware processor and operate in a computing environment to control one or more aspects of the device. A system of one or more computers can be configured to perform particular operations or actions by virtue of having software, firmware, hardware, or a combination of these installed on the system that in operation causes or cause the system to perform the actions. One or more computer programs can be configured to perform particular operations or actions by virtue of including instructions that, when executed by the data processing apparatus, cause the apparatus to perform the actions. One general aspect includes video processing and video transmission from the endoscopic retinaculatome to a client device. The system also includes a computing device that may include at least one hardware processor. The system also includes program instructions executable in the computing device that, when executed by the computing device, cause the computing device to: obtain video images, transmit video images, control white balance of the video, control zoom and focus of the camera, and control the light source. Other embodiments of this aspect include corresponding computer systems, apparatus, and computer programs recorded on one or more computer storage devices, each configured to perform the actions of the methods. In an example, the device can be configured to interface with augmented reality computing and video processing to allow a heads-up visualization of the endoscopic video content.

As shown in FIG. 1, an example endoscopic retinaculatome 100 includes a blade complex 102, a dilating head 104, a handle 106, and an arm 108 attached to a proximal end of the dilating head 104 such that the dilating head 104 is connected to the handle 106. The blade complex 102 includes a blade 110 configured to cut subcutaneous tissues and is detachably connected and replaceable. A scraper 112 is positioned on the dilating head 104 and configured to clean the fascia prior to the incision with the blade 110. The dilating head 104 also houses a camera 114 and a light source 116. For example, the camera 114 can be an imaging device having a lens 164 or imaging sensor positioned to provide a field of view. In this example, the camera 114 is retro-facing configured to provide a view of structures below the skin in front of the blade 110. In some examples, the camera 114 can be one or more cameras arranged in a forward-facing position, retro-facing position, or both to view of structures below the skin in front of the blade 110.

The handle 106 is configured to house components of the endoscopic retinaculatome 100 including a user interface 120, a controller 122, a video processor 124, a video transmitter 126, communication module 134, and a power source 128. In an example, the user interface 120 can be provided as physical controls on the handle 106 of the endoscopic retinaculatome 100 to provide commands to the controller 122 and/or operate the power source 128. The controller 122 is operatively connected to the camera 114 and the light source 116 via the arm 108 which is attached to the handle 106. The controller 122 interface with the communication module to transmit data to and receive data from a client device 130.

In some examples, the dilating head 104 is configured to be detachably connected to the arm 108 of the endoscopic retinaculatome 100. For example, the dilating head 104 can be mounted on the distal end of the arm 108 such that the dilating head 104 can be removed and replaced. For example, the dilating head 104 can be securely attached to the arm 108 by a coupler (not shown) such as threaded portions, slotted connector, detent, latch, or other means of secure attachment where the dilating head 104 and the arm 108 have respective mating features to securely mount the dilating head to the arm 108. Additionally, the coupler can have one or more connections to operatively connect the camera 114 and the light source 116 to components housed in the handle, such as the power source 128, controller 122, and the like. In an example, the dilating head 104 can be one of a plurality of dilating heads, where individual ones of the plurality of dilating heads can be specialized and configured with predetermined dimensions for particular types of surgeries. In another example, the replacement dilating head can be a dilating head having the same configuration as the head removed, or the replacement dilating head can be selected from another dilating head having at least some dimensions that are proportionally scaled to be smaller or larger than the dilating head being replaced.

In some examples, the dilating head 104 is attached to the arm 108 and the arm 108 is detachably attached to the handle 106. The arm 108 can have one or more connections to operatively connect the camera 114 and the light source 116 in the dilating head 104 to components housed in the handle, such as the power source 128, controller 122, and the like. The arm 108 can have a predefined length. Although shown with a straight arm in FIG. 1, the arm 108 can be configured with a bend. In some examples, the angle formed by the bend is adjustable like the reticulating arm of a gastrointestinal endoscope, which allows for superior visualization around angles. In some examples, the arm 108 of the endoscopic retinaculatome 100 is replicable with differing lengths and angles required for various anatomic locations where the device may be deployed. For example, the arm 108 can be threaded at the proximal end and received into a threaded seat of the handle 106 such that the dilating head 104 together with the arm 108 can be removed and replaced. While a threaded coupler is provided as an example, other means of secure attachment can be relied on to detachably connect the arm 108 to the handle 106. In some examples, the arm 108 and the dilating head 104 are both detachably attached to provide modular options to configure the endoscopic retinaculatome 100.

In an example, the endoscopic retinaculatome 100 can be included in a system or kit, where individual components constitute a functional unit for a given purpose and may be physically packaged together or separately. For example, an endoscopic retinaculatome kit or system can include a plurality of dilatating heads of different dimensions and size and/or different dilating heads configured with predetermined dimensions for a particular type of surgery. Individual dilating heads of the plurality of dilating heads can have the same type coupling to detachably connect to the arm of the endoscopic retinaculatome device. Similarly, in another example, an endoscopic instrument kit or system can include a plurality of dilatating heads of different dimensions and size and/or different dilating heads configured with predetermined dimensions for a particular type of surgery. Individual dilating heads of the plurality of dilating heads can have the same type coupling to detachably connect to the arm of the endoscopic retinaculatome device. For example, an endoscopic instrument system can comprise the endoscopic retinaculatome and a plurality of dilating heads, where the dilating head of the medical device is one of a plurality of dilating heads and replaceable. The individual ones of the plurality of dilating heads can be configured with predetermined dimensions and interchangeably attachable to the arm of the medical device. Similarly, in another example, various configurations of replaceable arms can be included in an endoscopic instrument kit or system. In some examples, the replaceable arms can include a dilating head in a one-piece unit. In some examples, both the replaceable arms and the dilating heads can be detachable.

The endoscopic retinaculatome 100 can be configured to interface with an external client device 130 provided with a display to view the images or video captured by the camera 114 in the dilating head 104. In one example, the client device 130 can be a device specifically configured for and designed to pair with the endoscopic retinaculatome 100 via a direct communication link. In another example, the client device 130 can be wirelessly connected to the endoscopic retinaculatome 100 via a secured network 132. In one example, the endoscopic retinaculatome 100 can have a port for a wired connection to a client device or monitor. For example, the endoscopic retinaculatome 100 can have a USB-C port, a mini-HDMI port, or another communication port suitable for video data transmission that can be utilized as an alternate video transmission path if a wireless connection is not available.

With reference to FIG. 1, the endoscopic retinaculatome 100 can comprise a computing environment embodied as a controller 122 and can be utilized in a networked environment is shown according to various embodiments. The networked environment can include the endoscopic retinaculatome 100 and a client device 130, which are in data communication with each other via a network. The network includes, for example, the Internet, intranets, extranets, wide area networks (WANs), local area networks (LANs), wired networks, wireless networks, or other suitable networks, etc., or any combination of two or more such networks. For example, such networks may comprise satellite networks, cable networks, Ethernet networks, and other types of networks.

The client device 130 can be at least one computing device comprising at least one hardware processor. The client device 130 can have program instructions stored in memory and executable by the client device that, when executed, direct the client device to access real-time video data from the camera of the medical device and display the real-time video data on a display. For example, the client device 130 can be a computing device provided by the user and configured with a program provided with instructions, when executed, that links the client device 130 with the endoscopic retinaculatome 100. For example, the client device 130 can be configured to display real-time video received from the camera 114 in the endoscopic retinaculatome 100 via the video transmitter 126. In some examples, the program executed by the client device 130 can also provide additional instructions to be executed by the controller 122 such as focus, image enhancement, magnification, white balance, contrast control, and the like. The controller 122 housed within the handle 106 can be electronically connected to the user interface 120, video processor 124, video transmitter 126, and power source 128, all also housed within the handle 106. The controller 122 can be a microprocessor or another computing device having software, firmware, hardware, or a combination thereof installed that when in operation causes or cause the controller to perform the actions. The controller 122 can be electronically connected to the camera 114 and light source 116 housed in the dilating head 104. The controller 122 can be configured to control the power to the camera 114 and light source 116. In some examples, the power source 128 is removable. In some examples, the power source 128 is rechargeable.

The controller 122 can be configured to operate the video processor 124 that receives the video images from the camera 114 and the video transmitter 126 that sends the video images to the client device 130. The video processor 124 can be configured to adjust white balance as well as control the zoom and focus features of the camera 114. In some examples, the video processor 124 can have a separate controller. In some examples, the video processor 124 can be integrated with or be a function of the controller 122. For example, the controller can be a system of one or more computing devices.

In some examples, the endoscopic retinaculatome 100 can have a communications module 134 to interface wirelessly via a direct communication link from the endoscopic retinaculatome 100 to a client device 130. In some examples, the endoscopic retinaculatome 100 can interface wirelessly with the client device 130 via a communication link on a secured network 132. In some exemplary embodiments, the communication link can be implemented through protocols such as ZigBee®, WiFi®, and Bluetooth®, or can be customized according to user requirements, which is not specifically limited in the exemplary embodiments. The endoscopic retinaculatome 100 can be configured for wireless integration, where the video signal can be obtained from the camera 114, processed by the video processor 124, and transmitted from the video transmitter 126 to a wireless client device 130. Wireless video transmission to the viewing tablet or client device allows the endoscopic retinaculatome 100 to be used independent of external wires and cables. The wireless video transmission to a client device 130 also allows the user the perform endoscopic surgery without the reliance on external video processing and the display of an endoscopic tower.

The user interface 120 can be provided as physical controls on the handle 106 of the endoscopic retinaculatome 100 to provide commands to the controller 122. The user interface 120 can be configured to operate the power source 128 and to control the camera 114 and light source 116 via the controller 122. For example, the user interface 120 allows the user to switch the light source 116 and camera 114 on or off. The controller 122 can be configured to allow the user to change lighting and video settings. In an example, the user interface 120 can also be configured to adjust the brightness of the light source 116 and focus of the camera 114. In another example, additional user control of the light source 116 and camera 114 can be provided remotely via the program executed on the client device 130. For example, the program executed on the client device can be configured to calibrate the light level for the environment.

Figure 2A:
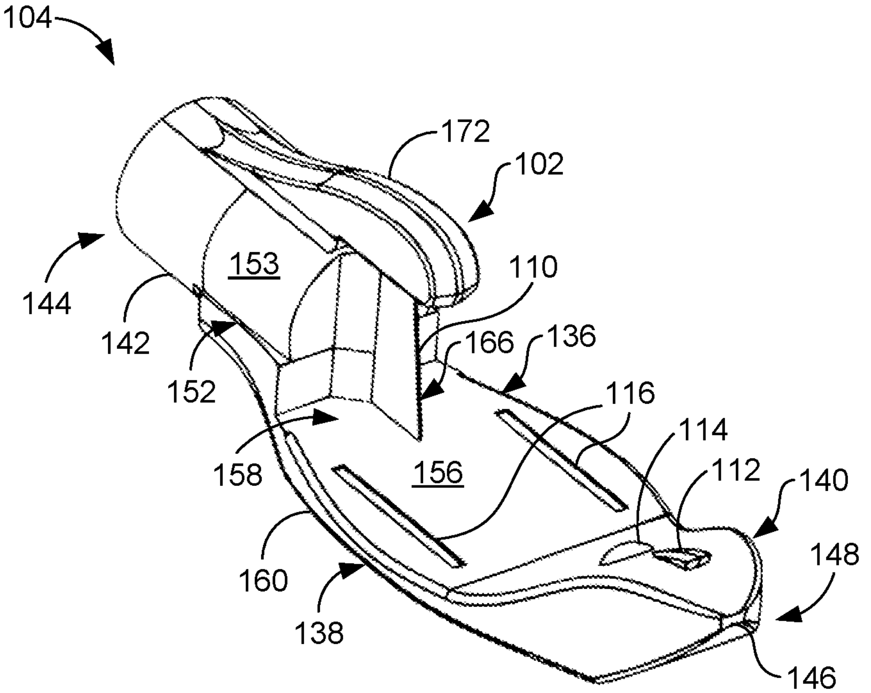
FIGS. 2A and 2B illustrate top and bottom views of an example dilating head of the endoscopic retinaculatome device in FIG. 1 according to various embodiments described herein.
Figure 2B:
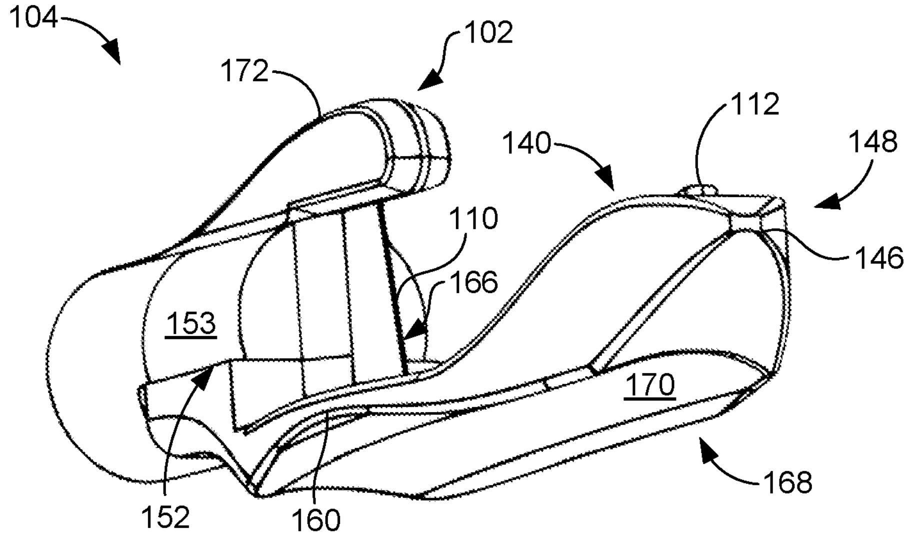

Shown in FIGS. 2A and 2B are top and bottom views of the dilating head 104 including the replaceable blade complex 102. The dilating head 104 includes a main body 136 configured to house a camera 114 and a light source 116. The main body 136 can include a base 138 and a distal portion 140 extending distally at an angle with respect to the base 138. The blade 110 extending onto the base 138 such that, when seated, the blade 110 is substantially perpendicular to the base 138 and the cutting edge 166 of the blade 110 faces the distal portion 140. In an example, the camera 114 can be positioned in the distal portion 140 and configured with a field of view of the cutting edge 166 of the blade 110. In another example, the camera 114 can be positioned in the main body 136 near the blade and facing the distal portion 140. For example, the camera 114 can be one or more cameras positioned in the main body 136 with a retro-facing field of view, a forward-facing field of view, or both.

The main body 136 of the dilating head 104 extends from a substantially cylindrical portion 142 at a proximal end 144 to a dilating tip 146 at the distal end 148 of the dilating head 104. The proximal end 144 being connected to the arm 108. The dilating tip 146 having a blunt tip at the distal end 148 and surfaces gradually extending outward over the distal portion 140 to join a base 138 of the main body 136. The distal portion 140 being contoured to provide a smooth transition to the base 138. The main body 136 comprises a blade seat 152 extending from the base 138 and a blade complex connector 154 (FIG. 3) formed at least in part in the substantially cylindrical portion 142 configured to removably receive and secure the replaceable blade complex 102. In this example, the blade complex 102 comprises a stabilizing section 153 configured to rest on a blade seat 152 of the base 138 when the blade complex 102 is seated and secured. As shown in FIGS. 2A and 2B, the blade complex 102 is seated in position for use. The blade 110 is centered in position on the base 138 of the main body 136 along a longitudinal axis extending from the proximal end 144, with the blade 110 defining a center plane of the dilating head 104.

The shape of the dilating head 104 including the dilating tip 146 allows the structures surrounding the subcutaneous tissue to be dilated free from the path of the device. In some examples, the dilating head 104 is contoured to hold soft tissue free of the lens 114. The dilating head 104 having symmetry about the center plane. The base 138 of the dilating head 104 has an upper surface 156 including a central portion 158 on which the blade 110 is partially seated or rests and a distal portion 140 that extends to the dilating tip 146. The central portion 158 of the upper surface 156 is at a distance from the longitudinal axis and can be substantially flat or have a slightly concave curvature laterally. The main body 136 can also include a pair of lateral fairings 160 extending laterally from the central portion 158 of the base 138. The pair of contoured lateral fairings 160 on opposite sides of the base 138 are symmetrical about the center plane.

The lateral fairings 160 provide a protective downward distraction of critical structures deep to the endoscopic retinaculatome 100. The light source 116 is housed within the main body 136 of the dilating head 104 and is configured to project light from the upper surface 156 to provide illumination without thermal damage to the tissue. In some examples, the light source 116 is a pair of light sources positioned symmetrically about the center plane. As shown in the example of FIG. 2A, the light source 116 can comprise two light strips on each side of the center plane. In some examples, the light source 116 can include at least one light emitting diode (LED) or at least one fiber optic strand.

The upper surface 156 extends from the central portion 158 to the distal portion 140. The distal portion 140 is configured at an angle such that the dilating tip 146 is substantially centered on the longitudinal axis. The camera 114 is housed within the main body 136 and configured such that the lens 164 of the camera 114 is positioned on the upper surface 156 of the distal portion 140 to have a field of view of at least the cutting edge 166 of the blade 110 and the space in front of it. For example, the camera 114 can be a high-definition camera with a fish-eye type lens. The camera 114 can be retro-facing such that the camera 114 has a view of any structures that may pass in front of the blade 110 as the dilating tip 146 is advanced. For example, the camera 114 allows the user to visually confirm that neurovascular structures are free of the cutting path of the blade 110. In other examples, the camera 114 can be positioned in the central portion 158 or another portion of the main body 136 to provide other views of zone in front of the blade 110. For example, the camera 114 can be forward facing.

An integral scraper 112 can be positioned on a superior surface of the distal portion 140. The scraper 112 is configured to clean the fascia prior to the incision with the blade 110, which allows for smoother operation. As shown in FIG. 2B, a lower surface 168 of the main body 136 is contoured including a concave surface 170 to keep neurovascular structures centered under the safety of the lateral fairings 160. At least a portion of the contoured lateral fairings 160 extend away from the blade seat 152 forming a concave surface 170 of the lower surface 168 of the main body 136. The concave surface 170 is configured to protect the adjacent neurovascular structures from the blade 110.

Figure 3:
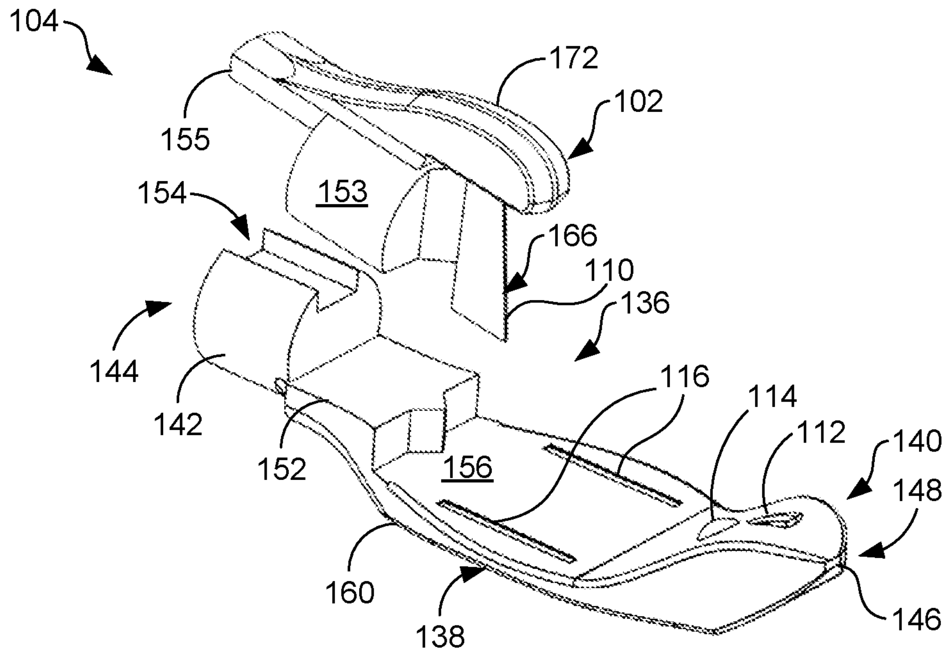
FIG. 3 illustrates a view of the detachable blade complex with respect to the seat of the dilating head of the endoscopic retinaculatome device in FIG. 1 according to various embodiments described herein.

As shown in FIG. 3, the dilating head 104 also includes a blade seat 152 configured to detachably receive and secure the blade complex 102 with the blade 110 defining a center plane of the dilating head 104. In this example, the blade complex 102 comprises a stabilizing section 153 configured to rest on a blade seat 152 of the base 138 and an attachment portion 155 configured to be received into the blade complex connector 154 and secured to the dilating head. The blade complex 102 comprises a blade 110 and a blade guard 172. The blade guard 172 of the blade complex 102 is contoured and configured to act as a spacer from the blade 110. The blade complex 102 can be detachably attached and is replaceable. The blade 110 is secured within the blade guard 172 such that a cutting edge 166 of the blade 110 is exposed. The blade guard 172 can have a superior portion that covers a top edge of the blade 110 and projects over the cutting edge 166 of the blade 110. The top edge of the blade being perpendicular to the cutting edge 166. The superior portion of the blade guard 172 limits inadvertent access to the cutting edge of the blade 110 and provides tactile feedback to the user as to the position of the blade. This blade complex 102 is designed to be a one-time use to ensure the sterility and sharpness of the blade. The blade 110 can be a razor blade or surgical blade configured to incise deep fascia or ligaments.

Figure 4:
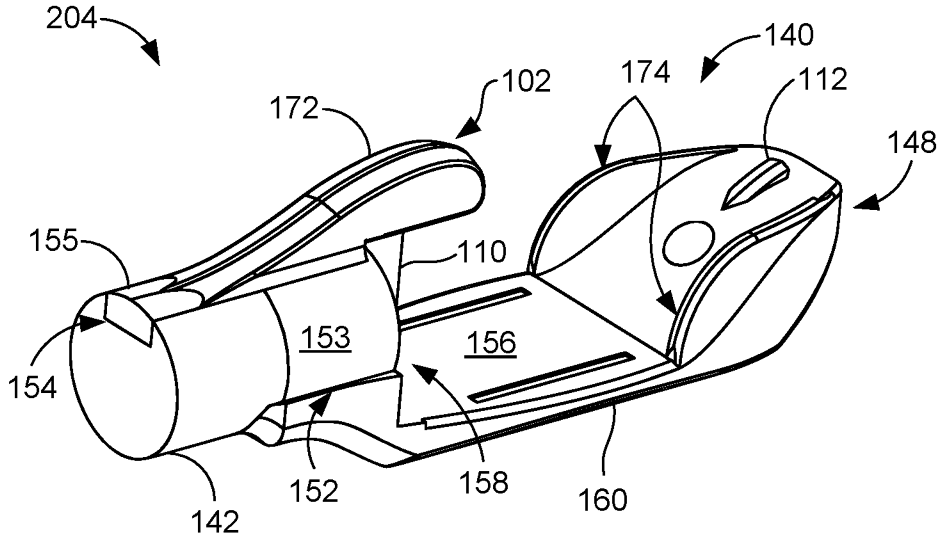
FIG. 4 illustrates an alternate example of a dilating head of the endoscopic retinaculatome device according to various embodiments described herein.

FIG. 4 shows an alternative dilating head 204 for endoscopic retinaculatome 100. In this example, the features of dilating head 204 are substantially the same as dilating head 104, having the same part numbers accordingly. In some examples, the dilating head 204 can be detachably connected to the arm 108 of the endoscopic retinaculatome 100 as previously described. The dilating head 204 has the additional feature of a pair of contoured flanges 174 protruding from the distal portion 140. The pair of contoured flanges 174 can be positioned on opposite sides of the distal portion 140 and symmetrical about the center plane. The pair of contoured flanges 174 can be configured to hold up soft tissue as the dilating head 204 is advanced. The pair of contoured flanges 174 can be shaped to gently curve away from the superior surface of the distal portion 140 from about the position of the scraper 112 to the base 138 of the dilating head 104. The pair of contoured flanges 174 can be made of a transparent material.

The endoscopic retinaculatome 100 can be fabricated using medical grade materials that can be sterilized. For example, the dilating head 104, the arm 108, and/or the handle 106 of the endoscopic retinaculatome 100 can have at least a portion formed from a medical grade polymer. Medical grade polymers are high wear, temperature resistant and corrosion resistant so that they can withstand frequent sterilization cycles. The endoscopic retinaculatome 100 can have a least a portion of the body formed from a transparent or translucent material. In an example, the base 138 of the dilating head 104 can be made of a transparent material such that the surgeon could see through the base and make sure that the important structures, such as nerves, and other critical structures to avoid, are below the device and not going to be cut by the blade. In another example, the base 138 can be provided with a window made of a transparent material such that the surgeon could see at least a portion of what is under the base 138. The controller 122, a video processor 124, a video transmitter 126 and other electronic components of the endoscopic retinaculatome 100 are configured such that the entire device can be sterilized. In some examples, the power source 128 can be removed before sterilization.

The above-described examples of the present disclosure are merely possible examples of implementations set forth for a clear understanding of the principles of the disclosure. Many variations and modifications can be made without departing substantially from the spirit and principles of the disclosure. All such modifications and variations are intended to be included herein within the scope of this disclosure and protected by the following claims.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

It is to be understood that, unless otherwise indicated, the present disclosure is not limited to particular materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Therefore, the following is claimed:

1. A medical device, comprising:

a blade complex comprising a blade and a blade guard, the blade secured within the blade guard such that a cutting edge of the blade is exposed, the blade guard having a superior portion that covers a top edge of the blade and projects over the cutting edge of the blade, the top edge of the blade being perpendicular to the cutting edge;

a dilating head comprising a main body having a blade seat, the main body configured to house a camera and a light source distal to the blade, the blade seat configured to receive a bottom edge of the blade and secure the blade complex with the blade defining a center plane of the dilating head and the blade being secured between the blade guard and the blade seat;

an arm attached to a proximal end of the dilating head; and a handle configured to house a controller, a video processor, a video transmitter, and a power source, the controller operatively connected to the camera and the light source via the arm attached to the handle.

2. The medical device of claim 1, wherein the main body comprises a base and a distal portion extending distally at an angle with respect to the base, at least a portion of the blade seat extending into the base such that, when seated, the blade is substantially perpendicular to the base and the cutting edge of the blade faces the distal portion, the camera being positioned in the distal portion configured with a field of view of the cutting edge of the blade.

3. The medical device of claim 2, wherein the distal portion comprises a distal tip having a blunt end, the distal portion being contoured to provide a smooth transition to the base of the main body.

4. The medical device of claim 2, wherein the distal portion further comprises a scraper on a superior surface of the distal portion.

5. The medical device of claim 2, wherein the main body further comprises a pair of fairings extending laterally from the base, the pair of contoured fairings on opposite sides of the base symmetrical about the center plane.

6. The medical device of claim 5, wherein at least a portion of the contoured fairings extend away from the blade seat forming a concave surface on the main body opposite the blade seat.

7. The medical device of claim 2, wherein the main body further comprises a pair of contoured flanges protruding from the base, the pair of contoured flanges positioned on opposite sides of the distal portion symmetrical about the center plane.

8. The medical device of claim 2, wherein the light source is a pair of light sources positioned symmetrically about the center plane.

9. The medical device of claim 1, wherein the light source is at least one LED or at least one fiber optic strand.

10. The medical device of claim 1, wherein the blade guard of the blade complex is contoured and configured to act as a spacer from the blade.

11. The medical device of claim 1, wherein the blade complex is detachably attached and replaceable.

12. The medical device of claim 1, wherein the dilating head is detachably attached to the arm.

13. The medical device of claim 12, further comprising a plurality of dilating heads, the dilating head of the medical device being one of a plurality of dilating heads and replaceable, individual ones of the plurality of dilating heads configured with predetermined dimensions and interchangeably attachable to the arm of the medical device.

14. The medical device of claim 1, wherein the dilating head is attached to the arm and the arm is detachably attached to the handle.

15. The medical device of claim 1, wherein the arm has a predefined length.

16. The medical device of claim 1, wherein the arm is configured with a bend.

17. The medical device of claim 1, wherein the controller is configured to operate the light source and the camera.

18. The medical device of claim 1, wherein the camera captures video and the video is transmitted wirelessly to a client device.

19. An endoscopic instrument kit, comprising:

the medical device of claim 1, and a plurality of dilating heads, the dilating head of the medical device being one of a plurality of dilating heads and replaceable, individual ones of the plurality of dilating heads configured with predetermined dimensions and interchangeably attachable to the arm of the medical device.

20. An endoscopic instrument system, comprising:

the medical device of claim 1, and at least one computing device comprising at least one hardware processor;

program instructions stored in memory and executable by the at least one computing device that, when executed, direct the at least one computing device to:

access real-time video data from the camera of the medical device; and display the real-time video data on a display.

* * * * *